United States Patent [19]

Israel et al.

[11] Patent Number: 4,900,664
[45] Date of Patent: Feb. 13, 1990

[54] REAGENT FOR DETECTION AND MEASUREMENT OF ACETALDEHYDE-PROTEIN CONDENSATES IN A FLUID, TOGETHER WITH ITS PREPARATION AND METHOD OF USE

[75] Inventors: Yedy Israel, Toronto, Canada; Ruth Arnon, Rehovot, Israel

[73] Assignee: Alcoholism and Drug Addition Research Foundation, Toronto, Canada

[21] Appl. No.: 914,326

[22] Filed: Oct. 2, 1986

[30] Foreign Application Priority Data

Oct. 4, 1985 [CA] Canada .................................. 492334

[51] Int. Cl.$^4$ ............................................. G01N 33/55
[52] U.S. Cl. ....................................... 435/7; 436/544; 436/548; 530/385; 530/402; 530/403; 530/406; 530/387; 424/85.8
[58] Field of Search ................. 435/7, 72.2, 68, 240.2; 436/67, 544, 547, 548, 811; 424/88, 85; 530/402, 403, 406, 385

[56] References Cited

U.S. PATENT DOCUMENTS

4,629,692 12/1986 Dean ........................................ 435/7
4,658,022 4/1987 Knowles et al. ..................... 530/402

OTHER PUBLICATIONS

Biological Abstract 85:96297.
Biological Report 33:96609.
Biological Report 33:82130.
Lancet, Sep. 10, 1983, p. 605.
Biological Abstract 85:68725.
Biological Report 32:90087.
Biological Abstract 83:29387.
Skinner et al., "Identification of Alcohol Abuse using Lab. Tests and a History of Trauma," Annals of Internal Med., vol. 101, pp. 847–851 (1984).
Nguyen & Peterson, "The Effect of Acetaldehyde Concs. on the Relative Rates of Formation of Acetaldehyde-Modified Hemoglobins," Proc. Soc. Exp. Biol. Med., vol. 177, pp. 226–233 (1984).
Stevens et al., "Acetaldehyde Adducts with Hemoglobin", J. Clin. Invest., vol. 67, pp. 361–369 (1981).
Israel et al., "Alcohol Abuse: Detection of Acetaldehyde Adducts in Rat Urine Following Administration of Erythrocytes Labelled With Radioactive Acetaldehyde", in 'Aldehyde Adducts in Alcoholism' (1985), Alan R. Liss, Inc. Publ., pp. 31–37.
Eshhar, "Monoclonal Antibody Strategy and Techniques", in 'Hybridoma Technology in the Biosciences and Medicine', Ed. T. Springer (1985), pp. 3–41.

*Primary Examiner*—Robert J. Warden
*Assistant Examiner*—Carol A. Spiegel
*Attorney, Agent, or Firm*—Bernard, Rothwell & Brown

[57] ABSTRACT

A method is provided for detecting and measuring acetaldehyde-protein condensates. An antibody is produced to an antigen, the antibody being cross-reactive with acetaldehyde-protein condensates, these condensates including protein moieties corresponding to or different from the protein moiety of the antigen. Detection and measurement of acetaldehyde-protein condensates may be performed by reacting the antibody with the acetaldehyde-protein condensate to form a complex and measuring the complex.

7 Claims, 7 Drawing Sheets

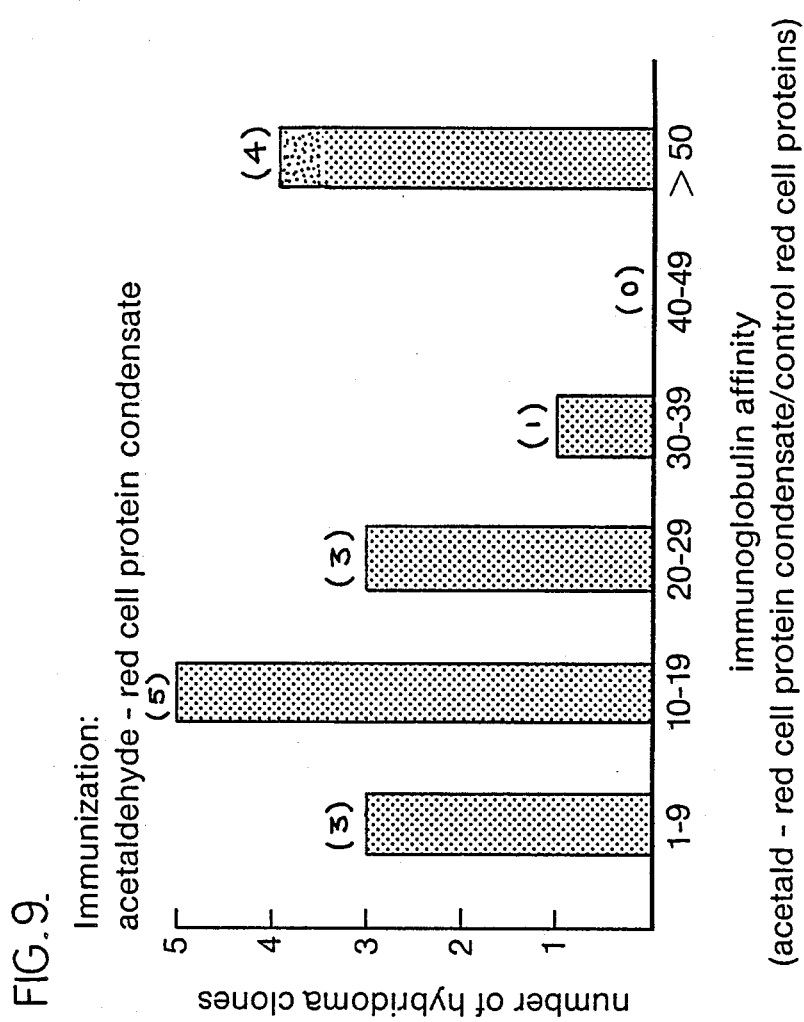

REAGENT FOR DETECTION AND MEASUREMENT OF ACETALDEHYDE-PROTEIN CONDENSATES IN A FLUID, TOGETHER WITH ITS PREPARATION AND METHOD OF USE

TECHNICAL FIELD OF THE INVENTION

This invention relates to the preparation of antibodies that recognize acetaldehyde-containing determinants of acetaldehyde-protein condensates and which are useful for detection and measurement of acetaldehyde-protein condensates in fluids and cells.

BACKGROUND OF THE INVENTION

The deleterious psychological, physical and social consequences of alcoholism are well documented. Thus an early identification of excessive alcohol consumption constitutes an important goal for society.

Present methods of diagnosis of excessive chronic alcohol consumption lack either specificity or sensitivity, or both. For example, fractures and general trauma from accidents which can aid in recognition of a hidden alcohol problem are not specific, since these can occur in many conditions and circumstances. In contrast, present laboratory tests such as the volume of red blood cells and the levels of certain serum enzymes have good specificity but are not sufficiently sensitive, since only a small fraction of individuals presenting for treatment of alcoholism have altered values in these tests: Skinner et al., Annals of Internal Med. 101: 847–851 (1984).

Acetaldehyde is a product of the metabolism of alcohol (ethanol) and is found in human blood after the ingestion of alcohol. Acetaldehyde is also known to bind covalently to proteins present in blood, both to plasma proteins and to proteins in red blood cells. Blood proteins are known to remain in the circulation for different periods of time, from days to weeks for plasma proteins and up to three months for red blood cell proteins.

Acetaldehyde levels in the blood of normal individuals are negligible, while blood levels of 20–100 $\mu$M acetaldehyde are seen in alcoholics. Even at these latter levels, however, only a minor amount of acetaldehyde binds to proteins, so that detection of the acetaldehyde-bound proteins is not possible with previously available techniques.

For proteins which remain for a long time in the blood, a sensitive method for measuring the levels of acetaldehyde-protein condensates present can provide a cumulative record of the amount and time of acetaldehyde exposure and therefore of the relative amounts of alcohol consumed over a period of time. Such methods as are available at present to detect reliably low levels of acetaldehyde-protein condensates utilise reaction of the protein with highly radioactive acetaldehyde (Nguyen & Peterson, Proc. Soc. Exp. Biol. Med., 177, 226–233, 1984; Stevens et al., J. Clin. Invest. 67, 361–369, 1981; Israel et al., in 'Aldehyde Adducts in Alcoholism', p. 31, 1985.) These methods are expensive, difficult to implement with facility, require special precautions and are clearly not applicable to measuring acetaldehyde-protein condensates generated in vivo in humans.

SUMMARY OF THE INVENTION

The present invention provides a sensitive and specific method for detecting and measuring acetaldehyde-protein condensates in a solution such as human blood lysates without the use of radiactive acetaldehyde. The method employs an antibody which is produced to an antigen, which antibody is characterized by being cross-reactive with a reactant selected from the group consisting of:

an acetaldehyde-first protein condensate;
an acetaldehyde-second protein condensate;
and an acetaldehyde-modified protein; wherein said acetaldehyde-first protein condensate comprises a first protein moiety corresponding to the protein moiety of said antigen;

said acetaldehyde-second protein condensate comprises a second protein moiety different to the protein moiety of said antigen; and said acetaldehyde-modified protein corresponding to said protein moiety of said antigen.

In an alternative embodiment, an antibody is produced to an antigen, which antibody is characterized by being cross-reactive to acetaldehyde-protein condensates which condensates include a protein moiety chosen from a group of protein moieties corresponding to or different from the protein moiety of said antigen.

DESCRIPTION OF THE INVENTION

The method of preparing antigens and antibodies in accordance with the present invention and the use of the latter in determining acetaldehyde-protein condensate levels in fluids will now be described by way of example and with reference to the drawings in which.

Figure 8:
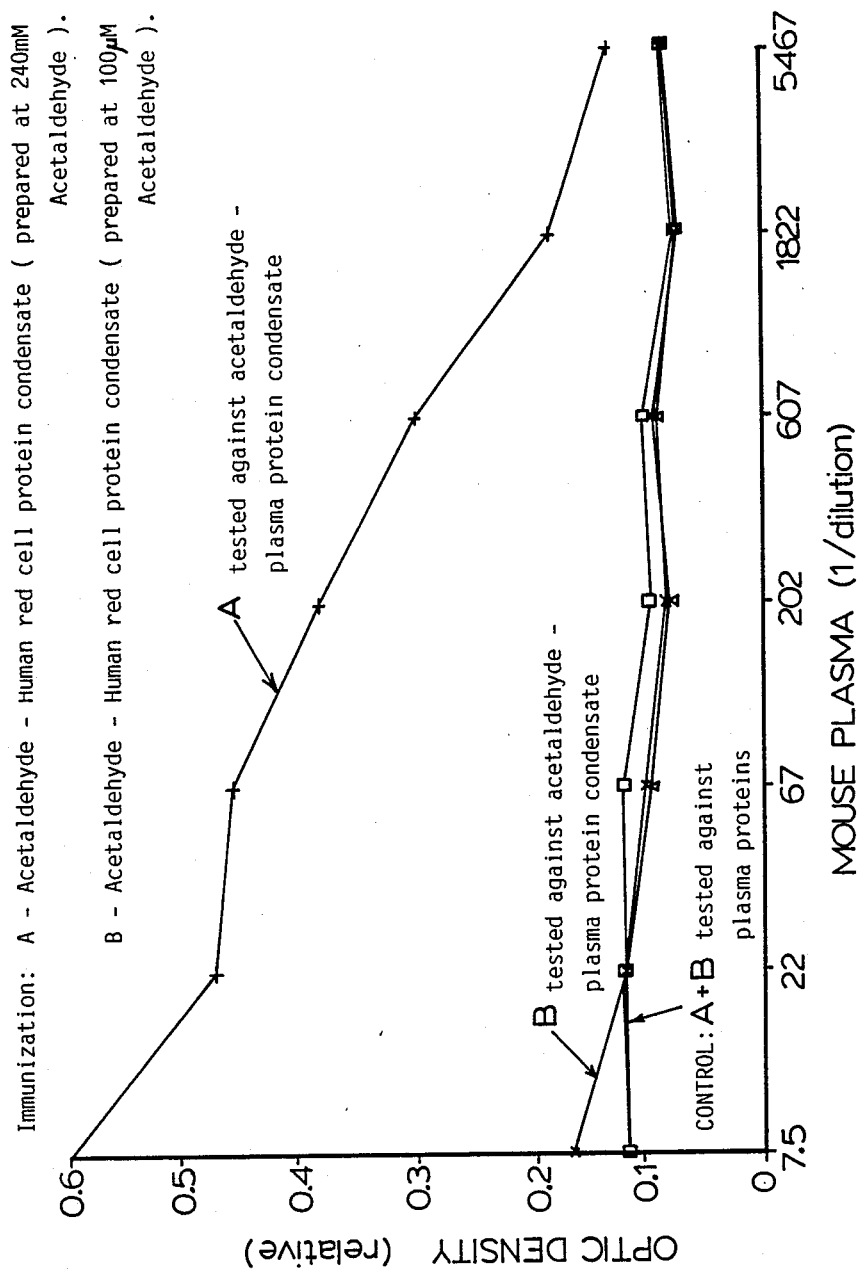

FIG. 8 is a graph showing the comparative potencies and cross-reactivities of a first antibody produced in response to an acetaldehyde-human red cell protein condensate prepared at a concentration of 100 μM acetaldehyde, and of a second antibody produced in response to an acetaldehyde-human red cell protein condensate prepared at a concentration of 240 mM acetaldehyde, towards acetaldehyde-human plasma protein condensate and towards human plasma protein.

FIG. 9 is a diagram illustrating the relative affinities of antibodies from a plurality of selected hybridoma clones, towards acetaldehyde-human red cell protein condensate and towards human red cell proteins and illustrates the isolation of clones synthesising immunoglobulins with very high specificity ratios.

Acetaldehyde-human red blood cell protein condensate was prepared as shown below in Example 1.

EXAMPLE 1

To human blood, Sodium Ethylenediaminetetraacetate (EDTA) was added to a final concentration of 5 mM and the mixture was centrifuged at 3000×g for 20 minutes. The plasma was removed and kept. The buffy coat above the red cells was sucked out and discarded. The red cells were washed with 10× their volume of 0.9% NaCl and recentrifuged three times. The final red cell pellet was lysed and the membranes extracted by the addition of 0.25 volumes of toluene followed by mixing for 30 minutes at 20° C. and centrifugation. Two ml of the lower aqueous phase, of which hemoglobin was the main protein constituent, were mixed at 20° C. with 2 ml phosphate buffered saline (PBS), pH 7.4, containing 480 mM acetaldehyde (Merck) and reaction was allowed to continue for 60 minutes. 272 mg sodium cyanoborohydride ($NaCNBH_3$) were added in 0.7 ml water and allowed to react for 30 minutes to reduce and stabilize the covalently bound acetaldehyde. The mixture was then dialyzed against 2 L of 1 mM $NaH_2PO_4$, pH 7.0, for 90 minutes, against a fresh 2 L of 1 mM $NaH_2PO_4$ for 16 hours and finally against 1 L of 1 mM $NaH_2PO_4$ for 24 hours. This treatment resulted in conversion of 96% of hemoglobin into fast hemoglobins, as determined by a Bio-Rad Kit (Bio-Rad Bulletin #4237, April, 1983). When the above procedure was carried out with omission of acetaldehyde to provide a control, 6–10% of the hemoglobin was found to chromatograph as fast hemoglobin.

It will be understood that for the purposes of this specification the term fast hemoglobins means conjugated hemoglobins which chromatograph in the Bio-Rad system like hemoglobins conjugated with glucose.

The foregoing example was repeated using $^3H$-labelled $NaCNBH_3$. The incorporation of acetaldehyde was estimated to be approximately 44 nmoles/mg protein.

When the red cell proteins were treated with 100 μM acetaldehyde, instead of 240 mM, less than 5% of the hemoglobin was converted to fast hemoglobin.

For the purposes of this specification, the condensates produced by treatment with 240 mM acetaldehyde will be termed heavily conjugated condensates.

Acetaldehyde-human plasma protein condensate was prepared as shown below in Example 2.

EXAMPLE 2

To 9 ml of human plasma was added 27 ml of saturated ammonium sulfate, pH 7.1, with mixing for 2 hours at 4° C. The precipitate, containing plasma proteins, was centrifuged at 10,000×g for 20 minutes. The pellet was dissolved in 18 ml of PBS and dialyzed at 4° C. against 1 L of half strength PBS for one hour. The medium was changed for fresh half strength PBS and dialysis continued for a further 18 hours. The final concentration was adjusted to 16 mg protein/ml. 5 ml of the above protein solution was added to 5 ml 480 mM acetaldehyde in PBS. The reaction was allowed to proceed for 60 minutes at 20° C., after which 700 mg $NaCNBH_3$, in 2 ml $H_2O$, were added. After 45 minutes, the mixture was dialyzed at 4° C. against 1 L PBS for 2 hours and subsequently against 5 L PBS for 18 hours.

The foregoing experiment was repeated using $^3H$-labelled $NaCNBH_3$. The acetaldehyde incorporated was estimated to be 726 nmoles/mg protein.

Acetaldehyde-keyhole limpet hemocyanin condensate was prepared as shown below in Example 3.

EXAMPLE 3

Keyhole limpet hemocyanin (KLH) (Calbiochem #374811 grade B) in saturated ammonium sulphate at a concentration 10 mg/ml, was dialyzed for 4 days at 4° C. against 4 L 5% $Na_2CO_3$ and for one day against PBS adjusted to pH 8.7. Two ml of KLH, 5 mg/ml, were mixed 2 ml 480 mM acetaldehyde at 20° C. After 60 minutes, 63 mg of $NaCNBH_3$ in 0.5 ml $H_2O$ was added, the mixture was allowed to stand for 3 hours and then dialyzed at 4° C. against 0.5 L PBS, pH 9.5, for 6 hours and thereafter against 2 L PBS, pH 9.5 for 10 hours at 4° C.

As mentioned previously, concentrations of acetaldehyde in alcoholics are in the range of 20 μM to 100 μM. To determine the cross-reactivity of antibodies generated in response to heavily conjugated aldehyde-protein condensates with condensates formed at acetaldehyde concentrations found in vivo, condensates were prepared as in Example 4.

EXAMPLE 4

2.5 ml of red cell lysate, diluted to 18 mg protein/ml, were dialyzed for 6 hours at 20° C. in closed flasks against 500 ml of 10 mM $NaCNBH_3$ in PBS containing either no acetaldehyde or 20 μM; 100 μM; 1.0 mM or 10 mM acetaldehyde. After this treatment total fast hemoglobins were: control (no acetaldehyde)=10.94%; 20 μM=12.09%; 100 μM=16.22%; 1 mM=49.6%; 10 mM=74.0%.

Acetaldehyde incorporation into proteins occurs to a greater degree if cyanoborohydride is added from the beginning of the process as above.

Polyclonal antibodies were prepared as described below, in Example 5.

EXAMPLE 5

Two month old female mice of the BALB-C×SJL, $F_1$ strain were injected subcutaneously with 100 μg of a protein-acetaldehyde condensate prepared as above, in a 1:1 volume suspension of saline containing 4 mg/ml protein and Freund's complete adjuvant. Four further injections were given at weekly intervals. The animals were then sacrificed by bleeding. The plasma was made 5 mM with respect to EDTA and used as reagent for the detection and measurement of acetaldehyde bound to proteins.

To select cell lines that produce immunoglobulins which react well with the acetaldehyde-containing epitopes of acetaldehyde-protein condensates but not with other epitopes in the condensate, the process of Example 6 was followed.

EXAMPLE 6

Spleen cells from immunized animals were hybridized with malignant myeloma cells according to the procedures described by Eshhar, *Hybridoma Technology in the Biosciences and Medicine*, T. Springer Ed., p. 3–41, Plenum Press, N.Y. (1985). Of 420 wells tested, 16 clones were found which reacted strongly with acetaldehyde-human red cell protein condensate and also reacted with acetaldehyde-human plasma protein condensate. Further culture of these cells yielded immunoglobulins with good affinities for the acetaldehyde-containing epitopes in acetaldehyde-human red cell protein condensates and which reacted very weakly or not at all with unmodified red cell proteins.

The measurement of the reaction between the antibodies and acetaldehyde-protein condensates and proteins was measured by means of an enzyme-linked second antibody immunoabsorbent assay (ELISA) using a sheep anti-mouse immunoglobulin linked to beta-galactosidase, as sold by the Amersham Co. (England) Cat N-831, except that gelatin 0.2% rather than bovine albumin was used to block nonspecific sites. The antigen used to coat the solid phase was in a volume of 100 $\mu$L at a concentration of 100 $\mu$g/ml. It will of course be appreciated that alternative techniques for detecting and measuring antigen-antibody combinations can be employed.

For example, radio immunoassay, affinity chromatography techniques, immunoelectrophoresis, fluoroimmunoassays, agglutination assays and complement-fixation assays may be used.

Figure 1:
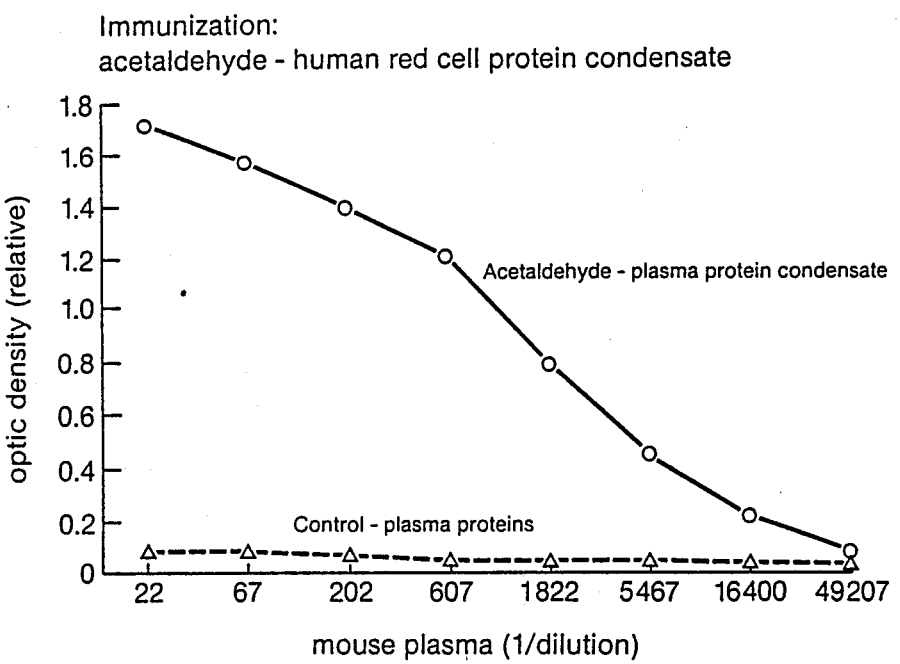
FIG. 1 is a graph showing cross-reactivity of an antibody produced in response to acetaldehyde-human red cell protein condensate towards acetaldehyde-human plasma protein condensates (0—0) and towards human plasma proteins (Δ—Δ)

It will be seen from FIG. 1 that immunization of mice as in Example 5, with acetaldehyde-human red cell protein condensate prepared s described in Example 1, yields plasma containing immunoglobulins that strongly react with acetaldehyde-human plasma protein condensate (Example 2) without reacting with plasma proteins that do not have bound acetaldehyde. Such immunoglobulins (antibodies) thus provide a specific reagent for recognition of the acetaldehyde moiety attached to only small epitopes in the plasma proteins.

Figure 2:
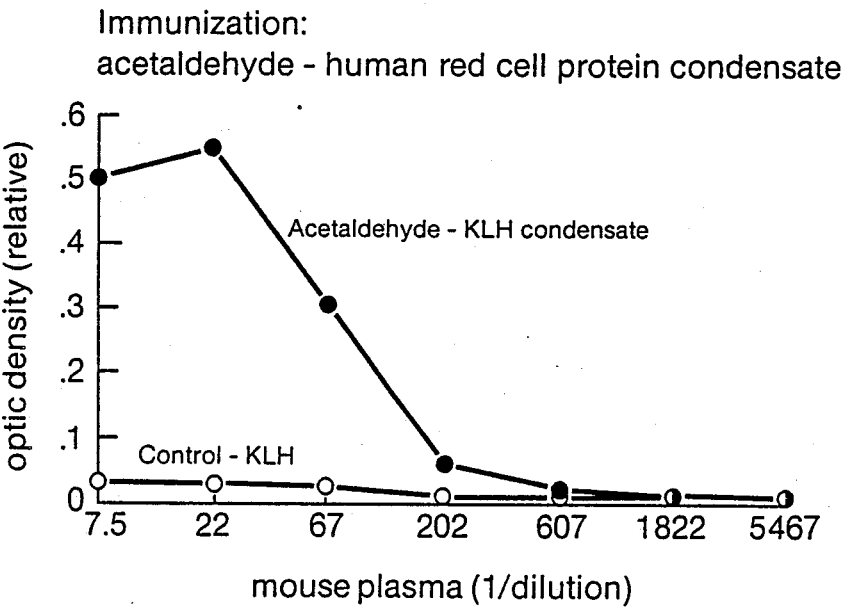
FIG. 2 is a graph showing the cross-reactivity of an antibody produced in response to acetaldehyde-human red cell protein condensate towards acetaldehyde-keyhole limpet hemocyanin (KLH) condensate (●—●) and towards keyhole limpet hemocyanin (KLH) (0—0).

As will be seen from FIG. 2, plasma of animals immunized with acetaldehyde-human red cell protein condensate also reacts with acetaldehyde-KLH condensate (Example 3) but it does not react with unmodified KLH. This indicates that the recognition of the acetaldehyde residue by the antibody is directed to a small epitope and is not species specific for the protein moiety.

Figure 3:
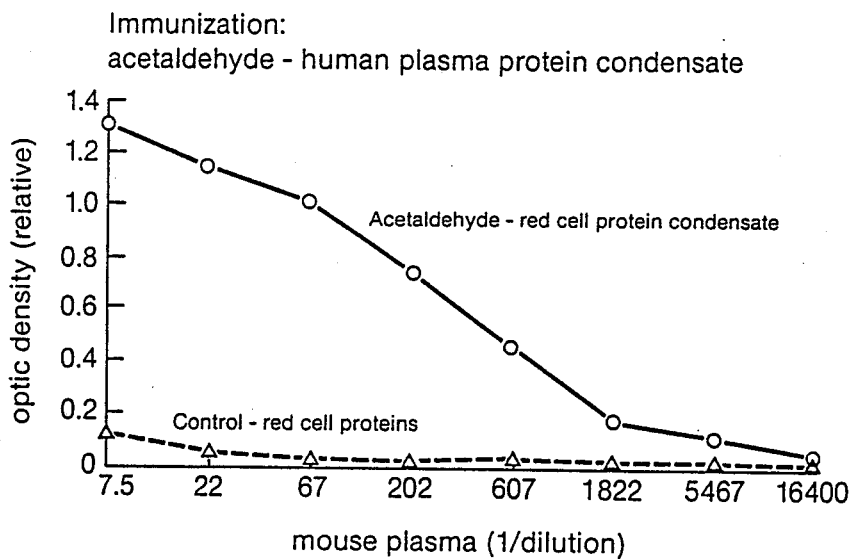
FIG. 3 is a graph showing the cross-reactivity of an antibody produced in response to acetaldehyde-human plasma protein condensate towards acetaldehyde-human red cell protein condensate (0—0) and towards human red cell proteins (Δ—Δ)
Figure 4:
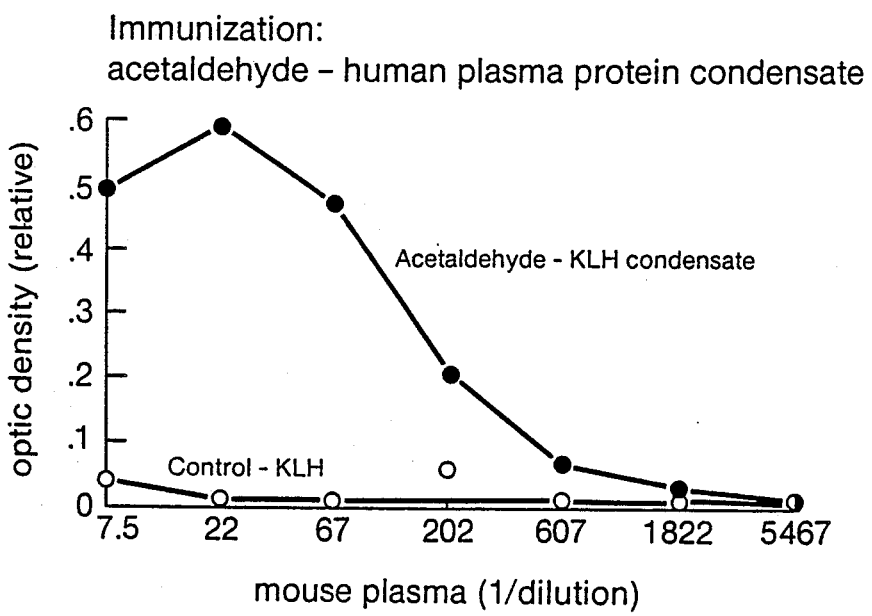
FIG. 4 is a graph showing the cross-reactivity of an antibody produced in response to acetaldehyde-human plasma protein condensate towards acetaldehyde-KLH condensate (●—●) and towards KLH (0—0)

As shown in FIGS. 3 and 4, mice immunized with acetaldehyde-human plasma protein condensate yielded immunoglobulins that strongly and specifically reacted with acetaldehyde-red cell protein condensate and with acetaldehyde-KLH condensate, but did not react with the respective unmodified proteins.

Figure 5:
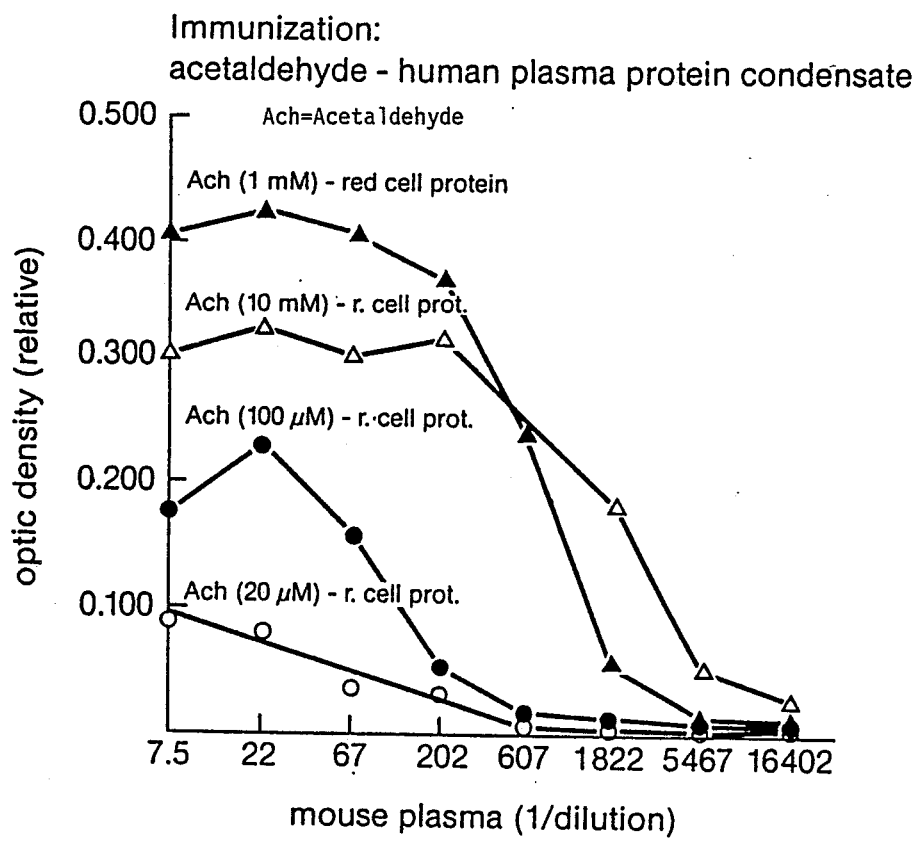
FIG. 5 is a graph showing cross-reactivity of an antibody produced in response to acetaldehyde-human plasma protein condensate towards a plurality of acetaldehyde-human red cell protein condensates produced at different concentrations of acetaldehyde. The abbreviation "Ach" in FIG. 5 stands for acetaldehyde.

FIG. 5 shows that the immunoglobulins generated after injection of heavily conjugated acetaldehyde-plasma protein condensates react well with acetaldehyde-red cell protein condensates formed at acetaldehyde concentrations of substantially 100 $\mu$m or less, within the range found in the blood of alcoholics, as in Example 4.

Figure 6:
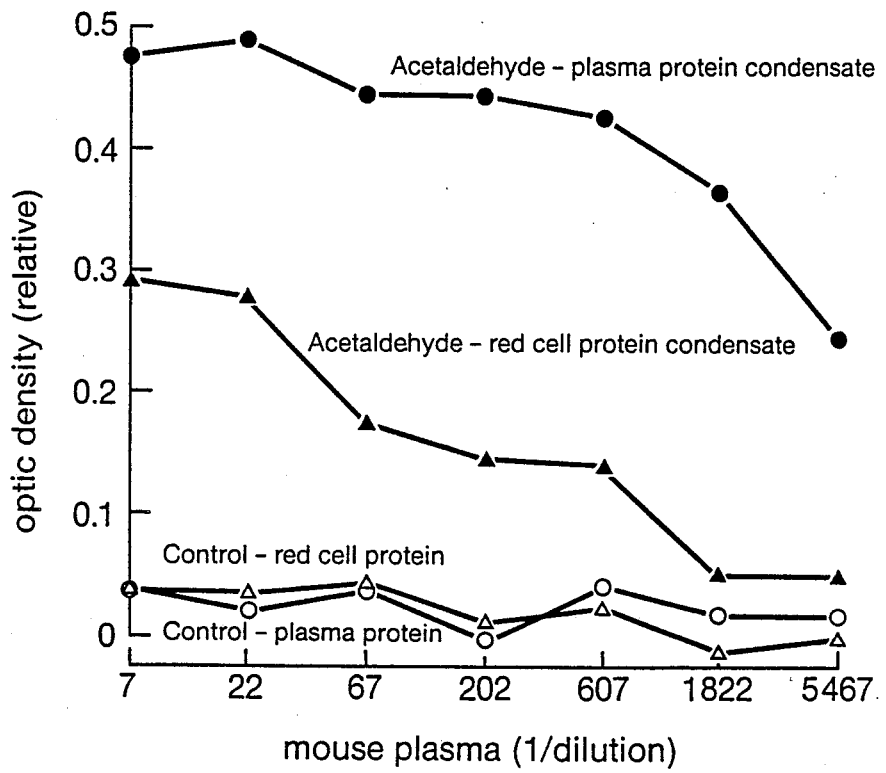
FIG. 6 is a graph showing the cross-reactivity of an antibody produced in response to acetaldehyde-KLH condensate towards various acetaldehyde-protein condensates and towards their corresponding proteins; it illustrates the recognition by the antibody of acetaldehyde-containing determinants in the protein-condensates and its lack of recognition of the corresponding proteins alone.

FIG. 6 shows that immunization with acetaldehyde-KLH condensate generates immunoglobulins reactive with both the acetaldehyde-plasma protein condensates and with the acetaldehyde-red cell protein condensates but not with their respective unmodified proteins.

Figure 7:
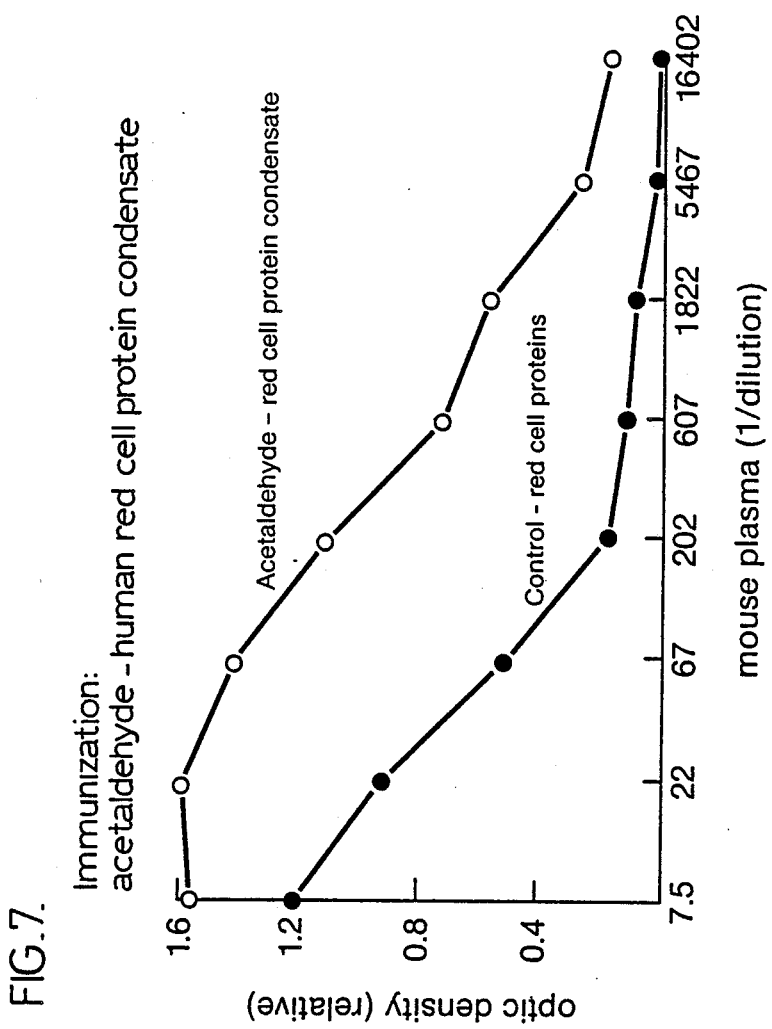
FIG. 7 is a graph showing the cross-reactivity of an antibody produced in response to acetaldehyde-human red cell protein condensate towards acetaldehyde-human red cell protein condensate and human red cell proteins, and serves to illustrate that the antibody has a higher potency for recognition of the condensate than for recognition of the unmodified red cell protein.

The plasma of animals immunized with acetaldehyde-red cell protein condensate reacts with both acetaldehyde-red cell protein condensate and with unmodified red cell proteins, but, as shown in FIG. 7, it is only 30–40% more active against the condensate.

FIG. 8 shows that the red cell protein condensate prepared at a concentration of acetaldehyde as found in the blood of alcoholics does not elicit a good immunological response as compared with the response to the heavily conjugated acetaldehyde-red cell proteins, produced by conjugation at an approximately 5000-fold greater concentration of acetaldehyde.

FIG. 9 illustrates the specificity ratio (binding affinity for acetaldehyde-red cell protein condensate/bind-affinity for red cell protein) of the immunoglobulins of sixteen selected hybridoma clones, selected as in Example 6. It can be seen that 25% of these hybridoma clones synthesized immunoglobulins with high specificity ratios, the cross-reactivity with condensate being at least fifty times the cross-reactivity with red cell protein.

From the foregoing, it will be noted that proteins heavily conjugated in vitro with acetaldehyde at a concentration within the range 150 to 300 mM generate, when injected chronically into animals, circulating antibodies that are able to recognize specifically and to quantify the acetaldehyde residue attached to proteins. The latter proteins may be different from the original protein injected.

It will also be noted that the antibodies generated by the above method are sensitive enough to react with proteins conjugated with acetaldehyde at the concentrations present in the blood of alcoholics, so that the acetaldehyde-protein condensate concentrations, and therefore the relative consumption of alcohol by an individual, may be determined.

Furthermore, immunoglobulin-producing spleen cells from animals chronically injected with acetaldehyde-protein condensates, when hybridized with myeloma cells and selected, yield cells which produce immunoglobulins with enhanced specificity of recognition for the acetaldehyde moiety bound to proteins.

What is claimed:

1. A method for the detection and quantification of an acetaldehyde-protein condensate comprising reacting said condensate with an antibody specific to an acetaldehyde-protein condensate antigen which antibody is characterized by being cross-reactive with a reactant selected from the group consisting of:
    an acetaldehyde-first protein condensate;
    an acetaldehyde-second protein condensate; and
    an acetaldehyde-modified protein, wherein said acetaldehyde-first protein condensate comprises a first protein moiety corresponding to the protein moiety of said antigen; and
    said acetaldehyde-second protein condensate comprises a second protein moiety different from the protein moiety of said antigen; and
    said acetaldehyde-modified protein corresponding to said protein moiety of said antigen, in order to form a complex; and measuring said complex, wherein the amount of said complex is a function of the concentration of the acetaldehyde-protein condensate present.

2. A method according to claim 1 wherein said complex is measured by means of an enzyme-linked second antibody immunoabsorbent assay system.

3. An antibody specific to an acetaldehyde-protein condensate antigen which antibody is characterized by being cross-reactive with a reactant selected from the group consisting of:

an acetaldehyde-first protein condensate;
an acetaldehyde-second protein condensate; and
an acetaldehyde-modified protein; wherein
said acetaldehyde-first protein condensate comprises a first protein moiety corresponding to the protein moiety of said antigen;
said acetaldehyde-second protein condensate comprises a second protein moiety different from said protein moiety of said antigen; and
said acetaldehyde-modified protein corresponding to said protein moiety of said antigen.

4. An antibody which recognises acetaldehyde-containing determinants of acetaldehyde-protein condensates.

5. A substantially immunologically pure antigen which stimulates the production of an antibody cross-reactive with acetaldehyde-protein condensates formed at acetaldehyde concentrations of substantially 100 $\mu$M or less.

6. A substantially immunologically pure antigen which comprises an acetaldehyde-protein condensate produced by the condensation of a protein with acetaldehyde at a concentration within the range 150 to 300 mM.

7. A substantially immunologically pure antigen which comprises an acetaldehyde-protein condensate, said condensate including a hemoglobin constituent which comprises 50–98% acetaldehyde-conjugated hemoglobin.

* * * * *